United States Patent [19]

Hoskins et al.

[11] 4,289,648
[45] Sep. 15, 1981

[54] BLOOD GAS CONTROLS COMPOSITION, METHOD AND APPARATUS

[75] Inventors: Michael K. Hoskins, Irvine; Gary D. Christiansen, Yorba Linda, both of Calif.

[73] Assignee: Ortho Diagnostics, Inc., Raritan, N.J.

[21] Appl. No.: 22,244

[22] Filed: Mar. 20, 1979

[51] Int. Cl.$^3$ .................. C09K 3/00; G01N 33/16; G01N 31/00

[52] U.S. Cl. .................. 252/408; 23/230 B; 23/232 R; 23/928; 206/305; 206/365; 206/524.1; 222/82; 422/61; 422/63; 422/83; 422/243; 128/2 G

[58] Field of Search .......... 252/408; 23/230 B, 232 R, 23/928; 422/61; 206/305, 524.1

[56] References Cited

U.S. PATENT DOCUMENTS

| | | | |
|---|---|---|---|
| 3,681,255 | 8/1972 | Wilfore | 252/408 |
| 3,973,913 | 8/1976 | Louderback | 252/408 |
| 4,001,142 | 1/1977 | Turner | 252/408 |
| 4,116,336 | 9/1978 | Sorensen et al. | 252/408 |
| 4,141,856 | 2/1979 | Dorwart, Jr. et al. | 252/408 |
| 4,163,734 | 8/1979 | Sorensen et al. | 252/408 |

OTHER PUBLICATIONS

Hackh's Chemical Dictionary, 4th Ed., McGraw-Hill Book Co., N.Y., p. 333, (Hydrogen Peroxide), (1969).

Primary Examiner—Teddy S. Gron
Attorney, Agent, or Firm—Geoffrey G. Dellenbaugh

[57] ABSTRACT

A hermetically sealed ampoule containing blood gas control fluid is provided wherein the fluid occupies the entire ampoule with no appreciable head space. The ampoule is provided with a plunger-like seal adapted to be directed against the contents of the ampoule and a pierceable seal through which may extend a hollow needle to act as a conduit for the contents upon expulsion from the ampoule. A syringe is also provided for expelling the contents from the ampoule.

18 Claims, 2 Drawing Figures

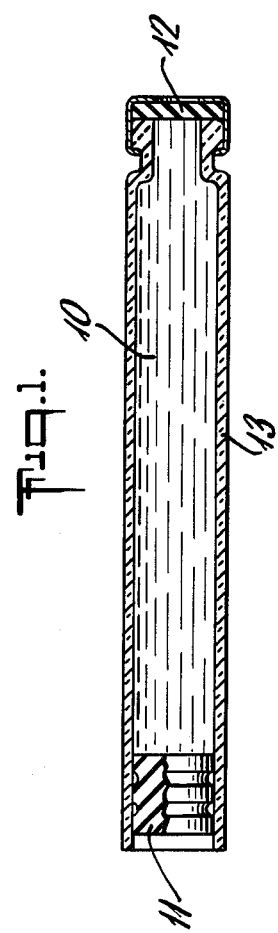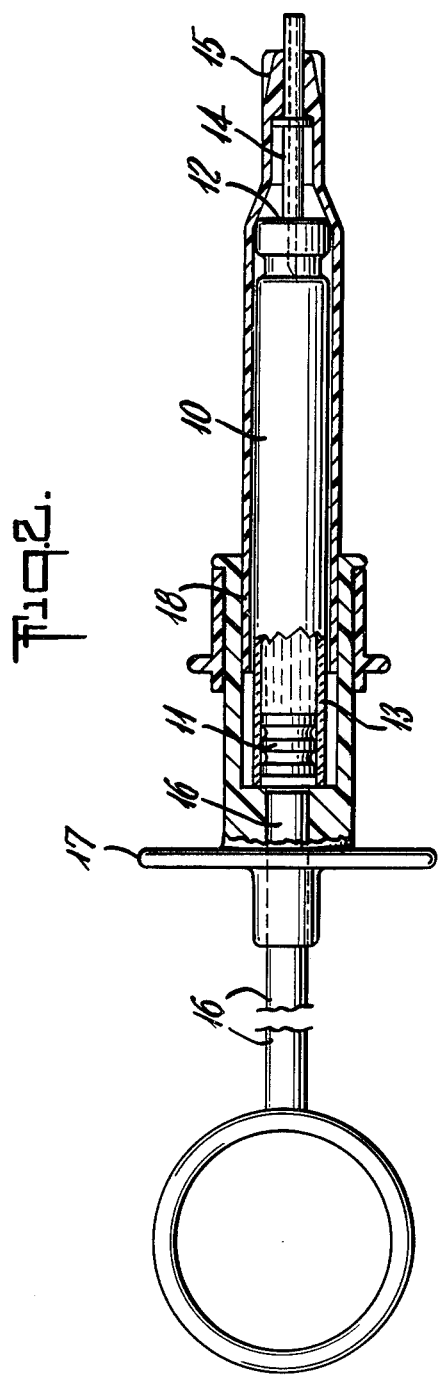

BLOOD GAS CONTROLS COMPOSITION, METHOD AND APPARATUS

TECHNICAL FIELD

This invention relates to blood gas controls and/or reference, standards and calibrating materials used in the determination of blood gases and blood pH.

In the field of diagnostic medicine, the determinations of blood pH, partial pressure of carbon dioxide ($pCO_2$) and/or bicarbonate ($HCO_3^-$) and partial pressure of oxygen ($pO_2$) are clinically important. These measurements are an indication of respiratory efficiency, renal function, efficacy of inhalation therapy and the like.

BACKGROUND OF THE INVENTION

The clinical laboratory has available to it a variety of instruments for conducting or performing these measurements. The difficulty in the prior art has been the challenge of supplying a reference or control material to compare the output of the instrument with that obtained on a sample of known constituency. For example, in the common blood analysis test that is performed, it is necessary to supply a standard sample having a known amount of the particular material that is being determined. Often, this standard is provided in various composition forms so that the results obtained on the instrument can be verified and correlated over a range of values.

In dealing with solid or dissolved materials such as protein, cholesterol, blood urea, enzymes and the like, it is usually a straightforward matter to supply as part of the reference solution a known amount of the particular material being determined. When one is seeking to determine pH, $pO_2$ and $pCO_2$ however, the situation is somewhat more complicated. The instrument itself is more complex because the nature of gas measurement requires the use of special electrodes and membranes. Any blood gas control, to be suitable, must be compatible with the electrodes and membranes. Since gases are involved, gas controls themselves cause problems because of the difficulty in supplying a liquid in which the known amounts of oxygen, carbon dioxide and the known value of pH are stable over significant periods of time. Various controls have been available and some of these are referred to later in the section on Prior Art. As used herein the terms "control", "reference solution" and "standard" are used to include fluids which may be used to verify values obtained from a blood gas-determining instrument on an unknown sample or which can be used as the calibrating material for that instrument. For example, in the usual situation, a sample of blood is introduced into the appropriate laboratory instrument and a value for a parameter, $pO_2$, for example, obtained. The technician does not know whether that value is correct for the sample introduced. If he introduces into the instrument a control material having a known value for $pO_2$, he can then compare the instrument read-out with the known value and determine whether or not the instrument is performing properly. On the other hand, that same control material can often be used as a calibrating fluid whereby the technician simply adjusts the reading obtained on the instrument to coincide with the known value of the control.

PRIOR ART

In utilizing instruments for blood gas measurements, it has been necessary to prepare a control immediately prior to the performance of the test because of the instability of the control material. The laboratory technician has had to meter the gases via a tonometer into a liquid and this liquid immediately used as the control or reference medium. Any delay subjects the liquid to absorbance of both carbon dioxide and oxygen from the atmosphere or vice versa, thereby altering the composition and reducing the reliability of the material as a control. This prior technique is quite burdensome, time consuming and expensive.

On the other hand, more recently, packaged controls have been made available for blood gas testing which are in sealed containers and which do not have to be prepared by the technician. These controls must be used immediately upon opening to the atmosphere and are still not entirely satisfactory in terms of reliability.

A variety of other blood gas control systems has been described in the art and reference will now be made to them briefly:

U.S. Pat. No. 4,001,142 issued on Jan. 4, 1977 relates to a blood gas control which contains a suitable dye, a triethanolamine-acetic acid buffer and sodium bicarbonate in equilibrium with a controlled atmosphere of oxygen, carbon dioxide and nitrogen.

U.S. Pat. No. 3,973,913 issued on Aug. 10, 1976 discloses a blood control standard which contains specially treated red cells and a gaseous head space over the buffered solution.

U.S. Pat. No. 3,874,850 issued on Apr. 1, 1975 discloses a method of analyzing for blood gas and utilizes equilibrating gas mixtures of known gaseous composition as the calibrating fluid.

U.S. Pat. No. 3,859,049 issued on Jan. 7, 1975 relates to a stable blood reference standard and control which contains a fluoride and an iodoacetate or a fluoroacetate.

U.S. Pat. No. 3,681,255 issued on Aug. 1, 1972 relates to aqueous bicarbonate solutions equilibrated with given concentrations of carbon dioxide-containing gases including oxygen.

U.S. Pat. No. 3,466,249 issued on Sept. 9, 1969 relates to a two vial system for a blood reference standard in which aqueous ammonium bicarbonate is used as the source of carbon dioxide and as a reconstituting material for the freeze dried blood serum contained in the first vial.

U.S. Pat. No. 3,224,445 issued on Dec. 21, 1965 relates to an aspirating syringe in which a movable plunger rod is provided with a barbed or spearpoint head for piercing the piston cork of a conventional disposable cartridge so that the cartridge is converted into an aspirating cartridge. This system is used, as described in the patent, for injecting pain killers into dental patients.

SUMMARY OF THE INVENTION

The present invention provides an aqueous blood gas control material useful over a range of the clinically significant values of pH, $pO_2$ and $pCO_2$; a novel composition of a control, which is not necessarily limited to a blood gas control, in a specially adapted ampoule; and a novel delivery system for delivering the control. In general, the blood gas control comprises a stabilized aqueous solution of carbon dioxide from a source such as a water soluble carbonate or bicarbonate or gaseous $CO_2$; a dissolved oxygen, preferably from a source such as a peroxide or gaseous $O_2$; optionally but preferably an agent to increase the surface tension of the liquid; and one or more of a water soluble buffer, said solution being compatible with the blood gas measuring electrodes and membranes.

The ampoule of the invention in which the control is packaged is a gas-impermeable container when the control is a blood gas control and preferably so when the control is other than a blood gas control. When used to contain a blood gas control, the ampoule is hermetically sealed and preferably has essentially no gaseous head space or bubbles. As used herein, the term "essentially no gaseous head space or bubbles" means the absence thereof to the naked eye assuming the container were clear to the transmission of light.

When used to contain a liquid other than a blood gas control, the ampoule need not be gas-impermeable but of course may be.

The present invention also includes a novel delivery system or syringe for delivering the control. A novel aspect of this system is that when used with the ampoule of the invention, the piston rod is not contiguous with the ampoule so that it is separate, apart and removable from the ampoule when in use. The syringe comprises a barrel portion having two ends, a piston action rod at one end of said barrel, and a fitting at the other end comprising a hollow needle extending into the barrel to communicate with and pierce the ampoule so as to extend into the contents of the ampoule.

BRIEF DESCRIPTION OF THE DRAWINGS

FIG. 1 shows one embodiment of the ampoule of the present invention.

FIG. 2 depicts the embodied ampoule within a syringe modified to fit blood gas instruments.

DETAILED DESCRIPTION OF THE INVENTION

The composition of the invention is comprised of the following:

an aqueous system containing dissolved carbon dioxide preferably from a water soluble carbonate or bicarbonate generally an alkali metal or alkaline earth metal carbonate or bicarbonate and most preferably sodium bicarbonate, or from having bubbled gaseous $CO_2$ into the mixture;

dissolved oxygen such as from, for example, gaseous oxygen, but preferably, a peroxide e.g. hydrogen peroxide or any water soluble or suspendible organic or inorganic peroxide which can release oxygen at a known rate and is in equilibrium at a known level of concentration with the liquid at a given temperature;

a water soluble buffer such as e.g. ethanolamine, tris buffer, or sodium or potassium mono or di-basic phosphates, and preferably a mixture of the mono and di-basic phosphates;

generally and preferably, an agent to increase the surface tension of the system such as the glycols with polyalkylene glycols and especially polyethylene glycol being preferred. Most preferred are those with molecular weights in the range of 5,000 to 15,000. Methyl cellulose and high molecular weight polysaccharides may also be used. The purpose of the agent is to retard absorption or diffusion of gases from the liquid during handling. A sufficient amount may be added to achieve this purpose;

optionally, a suitable quantity of sodium chloride to approximate isotonicity;

all in an aqueous system and having a pH in the range of 7.0–7.7 and preferably 7.1–7.6.

While the ranges of concentration of components supplied in the mixture are somewhat dependent upon the discretion of the individual supplying the controls, there is a range of values of generally accepted clinical scope. There are generally three levels of concentrations for controls that are required by the user; namely, a normal control and one each on the acid and base side of normal as those terms are used in this art. For example, the following ranges of the three parameters (at 37° C.) previously discussed are considered by most to be appropriate for a full range of control systems.

pH range = 7.0 to 7.7
$pCO_2$ range = 10 to 80 mm of mercury
$pO_2$ range = 30 to 170 mm of mercury The quantity of materials used to obtain values within this range for the most preferred components of the invention and other preferred parameters can be found from the table below. Adjustments to other levels, and for other ingredients may be made by those skilled in the art.

| Ingredient | General Range | Low Range | Normal Range | High Range |
|---|---|---|---|---|
| $NaHCO_3$ | 0.2–6 gms. | 0.2–1.0 gms. | 2–3 gms. | 5–6 gms. |
| $H_2O_2$[1] | 0.01–0.2 ml | 0.01–0.05 ml | 0.05–0.1 ml | 0.1–0.2 ml |
| NaCl | 1.5–2.0 gms. | 1.5–2.0 gms. | 1.5–2.0 gms. | 1.5–2.0 gms. |
| Polyethylene glycol | 10–100 gms. | 10–100 gms. | 10–100 gms. | 10–100 gms. |
| $NaH_2PO_4$ | 2–7 gms. | 7.0 gms. | 4.8 gms. | 2.2 gms. |
| $Na_2HOP_4$ | 10–15 mgms. | 10.2 mgms. | 12.4 mgms. | 15.0 mgms. |
| pH | 7.0–7.7 | 7.1 | 7.4 | 7.6 |
| Water | Q.S. to 1 liter | Q.S. to 1 liter | Q.S. to 1 liter | Q.S. to 1 liter |

[1] 30% aqueous solution.

In formulating the compositions of the invention, generally one prepares a composition comprising water, the buffer salts, and the optional ingredients, when used, and heats the mixture. The purpose of the heating is to remove the major portion of extraneous dissolved gases normally present in water including oxygen and carbon dioxide. In this regard, the oxygen level in water is usually around 160 mm Hg and this is, of course, too high for the normal and low control compositions. The heating step may be conducted at 70°–95° C. for periods ranging from 1 hour to 11 hours, and terminated when the desired level of $pO_2$ is reached. The preferred manner of treatment, however, is to continue the heating to well below the desired level, most preferably to a $pO_2$ of 30–40 mm Hg. At this point, the composition of the mixture can be adjusted to the desired $pO_2$ and $pCO_2$ levels by the addition of the peroxide or gaseous $O_2$, gaseous $CO_2$ or carbonate or bicarbonate. A source of hydronium ion, preferably from hydrochloric acid is then added to lower the pH, or hydroxyl ion preferably from sodium hydroxide, to raise it, to the desired level.

Once the composition is prepared, it is preferred to fill the control vessel while the composition is warm, but preferably not over 50° C. It has been discovered that when the filling operation is over 50° C., visible bubbles tend to form upon subsequent cooling. It is preferred therefore to fill at temperatures below 45° C.

In the filling operation and in fact in all operations subsequent to the heating step and prior to complete enclosure in the hermetically sealed container, the composition should not be exposed to the atmosphere.

The ampoule into which the composition of the invention is filled is non-gas permeable clear glass when gas controls are used. For other controls where gas permeability is no problem, clear plastic can be used. Preferred for use, is an ampoule which is a generally cylindrical tube fitted at one end with gas-tight and gas-impermeable plunger-like stopper capable of being moved against the contents of the tube. At the other end, is a gas-tight, gas-impermeable septum capable of being penetrated by a puncturing type device such as a hypodermic needle or a suitable micro electrode. Together, all of these elements cooperate to provide a sealed gas-impermeable ampoule containing a stabilized liquid mixture, preferably essentially free of bubbles or gaseous head space, and which can be expelled from the ampoule in a manner which substantially minimizes the possibility of exposure to external gas sources.

To expel the contents of the ampoule, the syringe of the present invention is preferably employed. The use of this syringe causes the pierceable septum to be pierced with a small diameter hypodermic needle or micro electrode which communicates with a fitting on the particular instrument being used. When appropriate, the plunger on the ampoule is depressed to expel the contents through the needle and into the instrument therein to be used immediately. The only gas that the contents come into contact with is the very small amount that is in the needle and the fitting. Ordinarily, this small a quantity of gas is in contact with the contents for only a few seconds, at most, and will have no deleterious effect on the composition of the control mixture.

The preferred apparatus for so doing, (expelling the contents of the ampoule,) is shown in the drawings.

FIG. 1 shows one embodiment of the ampoule of the present invention. The chamber is represented by 13 while 11 shows a gas-tight plunger made of gas-impermeable material such as butyl rubber and movable under pressure along the axis of the chamber and against the contents 10. Seal or septum 12 is pierceable by, for example, a hollow needle, such as a hypodermic needle which provides a conduit for the contents when the plunger 11 is directed under pressure against the contents of the chamber. Each of seals 11 and 12 are gas-tight and gas-impermeable seals ensuring the compositional integrity of contents 10.

As can be seen from FIG. 2, ampoule 13 is placed within a syringe 18 modified so as to fit most of the blood gas instruments available. The modification involves providing a fitting 15 having a hollow hypodermic needle 14 extending through it so as to engage and pierce at the appropriate time the pierceable septum 12 of the ampoule. Fitting 15 is adaptable so that various sized fittings can be used depending upon the blood gas instrument being used. In use, this fitting, while affixed to the syringe, is placed at the sampling port for receipt by the instrument of the control contents 10. Pressure is exerted by the hand on piston 16 so that plunger 11 is moved in the direction of the needle 14. The contents 10 are thus expressed through the needle 14 which, having pierced septum 12, provides the necessary conduit means to the blood gas instrument. Piston 16 has a non-piercing face, preferably a blunt end, and therefore is completely separate from the stopper on plunger 11.

The apparatus thus can be seen as comprising in combination, a barrel adapted to receive an ampoule, said barrel having two ends, one end being provided with a hollow needle, the other end being provided with a plunger. The needle end also is adapted to be connected to a suitable blood gas instrument.

What is claimed is:

1. A device comprising a hermetically sealed, gas-impermeable container containing a blood gas control liquid and having essentially no bubbles or gaseous head space, said liquid consists essentially of
    a. dissolved carbon dioxide in equilibrium with a water soluble carbonate or bicarbonate salt source in solution
    b. dissolved oxygen in equilibrium with a water soluble or water suspendible peroxide source in solution
    c. a water-soluble pH butter
    d. water
    e. said liquid having a pH of 7.0–7.7, a $pO_2$ of from 30–170 mm. Hg, and a $pCO_2$ of from 10–80 mm. Hg.

2. The device of claim 1 wherein the source of carbon dioxide is a bicarbonate.

3. The device of claim 1 wherein there is additionally present sodium chloride in a concentration of from 1.5 to 2.0 gms. per liter.

4. The device of claim 3 wherein the buffer comprises one or more of alkali metal mono or di-basic phosphate salts.

5. The device of claim 3 wherein the source of $CO_2$ is an alkali metal or alkaline earth metal bicarbonate.

6. The device of claim 3 wherein the source of oxygen is hydrogen peroxide.

7. The device of claim 4 wherein the phosphate salts are selected from one or more of sodium monobasic phosphate, sodium di-basic phosphate, potassium monobasic phosphate, potassium di-basic phosphate and mixtures thereof.

8. The device of claim 1 wherein the carbon dioxide source is sodium bicarbonate and the oxygen source is hydrogen peroxide.

9. The device of claim 7 wherein said container is essentially clear to the transmission of light thereby permitting visual inspection of said composition.

10. A blood gas control composition which consists essentially of
    (a) water
    (b) dissolved $CO_2$ in equilibrium with a water-soluble carbonate or bicarbonate salt source in solution
    (c) dissolved oxygen in equilibrium with a water soluble or water suspendible peroxide source in solution
    (d) a water soluble pH buffer
    (e) said composition having a pH of 7.0–7.7, a $pO_2$ of from 30 to 170 mm Hg, and a $pCO_2$ of from 10 to 80 mm Hg 11. The composition of claim 10 wherein the source of oxygen is hydrogen peroxide and the dissolved $CO_2$ is an alkali metal or alkaline earth metal carbonate or bicarbonate.

12. The composition of claim 11 wherein the buffer comprises one or more of alkali metal mono and di-basic phosphate salts.

13. The composition of claim 10 wherein the composition has a pH of from 7.1 to 7.6.

14. The composition of claim 10 additionally containing an agent to increase the surface tension of the composition and retard absorption or diffusion of gases from the composition during handling.

15. The composition of claim 14 wherein said agent is a polyethylene glycol.

16. The composition of claim 10 additionally containing sodium chloride in a concentration of from 1.5 to 2.0 gms. per liter.

17. The device of claim 1 wherein the liquid additionally contains an agent to increase the surface tension of the liquid and retard absorption or diffusion of gases from the liquid during handling.

18. The device of claim 17 wherein said agent is a polyethylene glycol.

* * * * *